(12) United States Patent
Brown

(10) Patent No.: US 9,212,962 B2
(45) Date of Patent: Dec. 15, 2015

(54) SELF-POWERED PRESSURE SENSOR ASSEMBLY

(71) Applicants: Robert Bosch Healthcare Systems, Inc., Palo Alto, CA (US); Robert Bosch GmbH, Stuttgart (DE)

(72) Inventor: Stephen J. Brown, Woodside, NJ (US)

(73) Assignee: Robert Bosch GmbH, Stuttgart (DE)

( * ) Notice: Subject to any disclaimer, the term of this patent is extended or adjusted under 35 U.S.C. 154(b) by 340 days.

(21) Appl. No.: 13/939,944

(22) Filed: Jul. 11, 2013

(65) Prior Publication Data

US 2014/0013852 A1 Jan. 16, 2014

Related U.S. Application Data

(60) Provisional application No. 61/670,310, filed on Jul. 11, 2012.

(51) Int. Cl.
| | |
|---|---|
| *G01L 7/00* | (2006.01) |
| *A61B 5/02* | (2006.01) |
| *G01L 19/00* | (2006.01) |
| *G01L 19/08* | (2006.01) |
| *A61B 5/0215* | (2006.01) |
| *H02N 2/18* | (2006.01) |
| *A61B 5/00* | (2006.01) |

(52) U.S. Cl.
CPC ........... *G01L 19/0092* (2013.01); *A61B 5/0215* (2013.01); *G01L 19/086* (2013.01); *H02N 2/181* (2013.01); *A61B 5/0031* (2013.01); *A61B 2560/0214* (2013.01); *A61B 2562/0219* (2013.01)

(58) Field of Classification Search
None
See application file for complete search history.

(56) References Cited

U.S. PATENT DOCUMENTS

| | | | | |
|---|---|---|---|---|
| 5,197,467 | A * | 3/1993 | Steinhaus et al. | 607/20 |
| 6,979,995 | B2 * | 12/2005 | Horio et al. | 324/76.48 |
| 6,996,627 | B1 | 2/2006 | Carden | |
| 7,007,040 | B1 | 2/2006 | Duke et al. | |
| 7,179,229 | B1 * | 2/2007 | Koh | 600/485 |
| 7,706,881 | B1 * | 4/2010 | Benser | 607/24 |
| 7,970,620 | B2 | 6/2011 | Brown | |

(Continued)

FOREIGN PATENT DOCUMENTS

WO    2010058086 A1    5/2010

OTHER PUBLICATIONS

International Search Report and Written Opinion corresponding to PCT Application No. PCT/US2013/050124, mailed Feb. 3, 2014 (9 pages).

*Primary Examiner* — Peter Macchiarolo
*Assistant Examiner* — Jermaine Jenkins
(74) *Attorney, Agent, or Firm* — Maginot Moore & Beck LLP

(57) ABSTRACT

In one embodiment, a pressure sensor assembly includes an accelerometer configured to produce a first current upon movement of the accelerometer, a capacitor configured to receive the first current thereby charging the capacitor, a gate element operably connected to the capacitor and configured to discharge a second current from the capacitor upon the capacitor attaining a threshold voltage, a pressure sensor configured to receive the discharged current to produce a first signal corresponding to at least one pressure reading of the pressure sensor, and a transmitter operably connected to the pressure sensor and configured to transmit a second signal based upon the first signal to an external device configured to store data corresponding to the second signal.

20 Claims, 3 Drawing Sheets

(56) References Cited

U.S. PATENT DOCUMENTS

| | | | |
|---|---|---|---|
| 7,970,734 B2 * | 6/2011 | Townsend et al. | 707/602 |
| 8,388,670 B1 * | 3/2013 | Zou et al. | 607/112 |
| 8,475,370 B2 * | 7/2013 | McCombie et al. | 600/301 |
| 2004/0225730 A1 | 11/2004 | Brown et al. | |
| 2006/0235723 A1 | 10/2006 | Millard | |
| 2007/0276270 A1 | 11/2007 | Tran | |
| 2010/0298720 A1 | 11/2010 | Potkay | |
| 2014/0018643 A1 * | 1/2014 | Achkar et al. | 600/302 |

* cited by examiner

SELF-POWERED PRESSURE SENSOR ASSEMBLY

This application claims the benefit of U.S. Provisional Application No. 61/670,310 filed Jul. 11, 2012, the entire contents of which is herein incorporated by reference.

FIELD OF THE INVENTION

This disclosure relates to pressure transmitters and, more particularly, to a self-powered pressure transmitter for an objective measurement of pressure.

BACKGROUND

Monitoring of blood pressure by caregivers has become a well-established bio-monitoring tool. Knowledge of a patient's blood pressure is often essential to properly assess the patient's medical condition. Hypertension, hypotension, and shock are some examples of conditions monitored via blood pressure. Frequently, a sphygmomanometer (an instrument, often attached to an inflatable air-bladder cuff and used with a stethoscope, for measuring blood pressure in an artery) is used for such monitoring.

Continuous monitoring of the blood pressure enables medical personnel to immediately detect changes in the cardiovascular system indicating stress, and to respond rapidly with the appropriate action. While a sphygmomanometer is effective, continuous use of a sphygmomanometer is inconvenient. Accordingly, various approaches for continuous monitoring of blood pressure have been developed. One common approach involves inserting a needle into the artery or vein of a patient and exposing a catheter to the fluid pressure in the artery or vein. A sterile solution fills the catheter and the pressure of the cardiovascular system at that point in the body is transmitted through the sterile solution to a fluid pressure sensing device connected to the catheter outside the patient's body. A pressure-sensing device such as a pressure transducer is then used to produce an electric signal proportional to the fluid pressure of the blood at the open end of the catheter. While this type of system is useful when an individual is substantially immobilized, it is not useful for patients who are not confined to a bed.

One approach that overcomes some of the limitations of the above systems is the use of an implantable pressure monitor. U.S. Patent Publication Number 2004/0193058 describes an implantable pressure monitor. While the device in the '058 publication measures the blood pressure of an individual, the '058 device does not provide information as to the context of the particular blood pressure reading. For example, while a given blood pressure may be acceptable during and shortly after heavy exercise, that same blood pressure while an individual has been at rest for a period of time may indicate a problem in the individual.

Therefore, an improved implantable blood pressure sensor is needed. It would be advantageous if the blood pressure sensor provided insight as to the context of a particular blood pressure reading. A system which did not require external power sources to operate would be further beneficial.

SUMMARY

The embodiments herein provide a device and method for measuring blood pressure of a body while providing context of the blood pressure reading. In one embodiment, an implantable pressure sensor assembly includes an accelerometer that produces current as an individual moves. The produced current charges a capacitor. When the capacitor is charged to a predetermined threshold, a gate element automatically discharges the capacitor. The discharged current is directed to a pressure sensor which detects the blood pressure of the individual and generates a signal associated with the detected blood pressure. The accelerometer thus produces the power used by the implantable pressure sensor assembly. Additionally, the period required to charge the capacitor is directly related to the amount of activity of the user. Thus, more pressure readings are obtained as the activity of the user increases. The frequency of the readings is thus directly related to the activity level of the individual.

In another embodiment, a pressure sensor assembly includes an accelerometer configured to produce a first current upon movement of the accelerometer, a capacitor configured to receive the first current thereby charging the capacitor, a gate element operably connected to the capacitor and configured to discharge a second current from the capacitor upon the capacitor attaining a threshold voltage, a pressure sensor configured to receive the discharged current to produce a first signal corresponding to at least one pressure reading of the pressure sensor, and a transmitter operably connected to the pressure sensor and configured to transmit a second signal based upon the first signal to an external device configured to store data corresponding to the second signal.

In yet another embodiment, a method for measuring blood pressure by a pressure sensing assembly, includes attaching a pressure sensing assembly with an accelerometer to an individual, producing a first current with the accelerometer, charging a capacitor with the first current, automatically discharging a second current from the capacitor with a gate element when the capacitor reaches a predetermined voltage, powering a pressure sensor with the second current to generate a first signal associated with at least one first pressure sensed by the pressure sensor, transmitting a second signal based upon the first signal to an external device, and storing the second signal at the external device.

In some embodiments an RFID (Radio frequency identification) element is provided within the pressure sensor assembly. The RFID provides a unique identification code for the pressure sensor assembly. Accordingly, when the pressure sensor assembly transmits a pressure reading signal to an external receiver, the unique identification code is also transmitted.

In some embodiments, a system includes an external device which receives the signal transmitted by the pressure sensor assembly. The external device stores and displays the received data. The external device can be used to provide feedback to the user of the user's activity level and associated blood pressure.

In one embodiment, a method for measuring blood pressure with a pressure sensor assembly includes producing a current using an accelerometer. The produced current is used to charge a capacitor. A gate element automatically discharges the capacitor when the capacitor is charged to a predetermined threshold. Current from the capacitor is used to power a pressure sensor which generates a signal associated with a measured pressure. The generated signal, along with identification data of the pressure sensor assembly is transmitted from the pressure sensor assembly to an external device. The external device stores and displays received blood pressure data along with data indicating the activity level of the user.

Other features of the embodiments herein will be apparent from the drawings, and detailed description that follows below

DESCRIPTION

Figure 1:
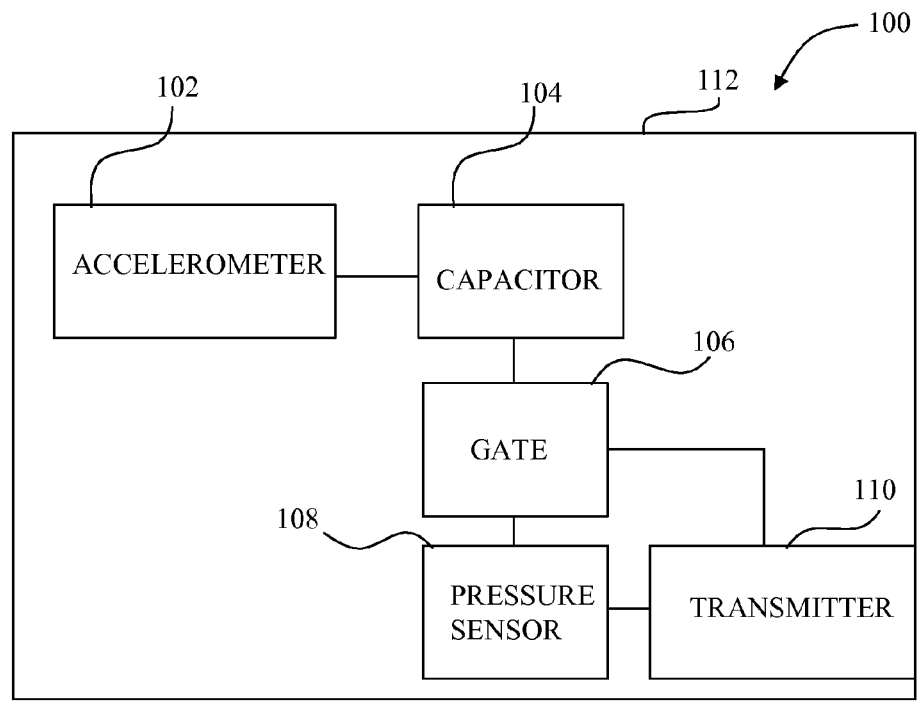
FIG. 1 depicts a block diagram illustrating an implantable pressure sensor assembly according to one embodiment of the disclosure.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

FIG. 1 illustrates a general block diagram of a pressure sensor assembly 100. The pressure sensor assembly 100 includes an accelerometer 102, a capacitor 104, a gate element 106, a pressure sensor 108, and an RF transmitter 110. The accelerometer 102, capacitor 104, gate element 106, pressure sensor 108, and RF transmitter 110 are positioned within a housing 112. The housing 112 is constructed of biologically compatible material and is hermetically sealed. Accordingly, the pressure sensor assembly 100 can be implanted into an individual.

The accelerometer 102 is configured to generate an electrical current upon movement of the accelerometer. The accelerometer 102 in one embodiment is a tri-axial accelerometer configured such that changes in movement along any of its three coordinate axes produces electrical current. More specifically, a change in momentum of the accelerometer 102 results in a burst of current. Accordingly, when the pressure sensor assembly 100 is implanted in an individual, or even borne by an individual, changes in momentum of the individual result in generation of electrical current. The electric current produced by the accelerometer 102 is thus substantially proportional to the activity of the individual. To with, as the individual is more active, more bursts of electrical current are produced.

The electric current produced by the accelerometer 102 is directed to an energy storage device which in this embodiment is capacitor 104. The bursts of current from the accelerometer thus charge the capacitor 104. The rate at which the capacitor 104 is charged is directly related to the rate at which electric current is produced by the accelerometer 102. Accordingly, as an individual's activity increases, the capacitor is charged more quickly.

The gate element 106 is configured to initially electrically isolate the capacitor 104 from the elements of the pressure sensor assembly 100 other than the accelerometer 102. When the charge of the capacitor 104 reaches a predetermined threshold, the gate element 106 is configured to discharge the capacitor 104 by electrically connecting the pressure sensor 108 and the transmitter 110 to the capacitor 104. The gate element 106 in some embodiments is s a diode and in other embodiments is configured to operate a switch to provide discharge of the capacitor 104.

The gate element 106 thus discharges the capacitor 104 whenever the capacitor 104 is charged to the threshold voltage. Because the rate at which the capacitor 102 is charged is related to the activity level of the individual, the frequency at which the capacitor 104 is discharged is also related to the activity level of the individual.

The discharging capacitor 104 provides a periodic current that powers the pressure sensor 108. The pressure sensor 108 is a low power sensor which, upon energization, generates a signal associated with a sensed pressure. Depending upon the particular configuration of the system, the signal may include data associated with a discrete pressure or data associated with pressure over a short time span. Consequently, the data may include a full cycle of pressure data. A "full cycle" of pressure data means sufficient pressure data to capture the highest value of a cyclical pressure and the lowest value of the cyclical pressure, e.g., one cardiac cycle.

The signal associated with a sensed pressure is passed to the transmitter 110 which is also powered by the discharging capacitor 104 in this embodiment. The transmitter 110 transmits a signal including the pressure data. In some embodiments a full cycle of pressure data is transmitted. In other embodiments, only an instantaneous pressure data is transmitted.

In any event, each time the capacitor reaches the threshold voltage, a transmission occurs. Therefore, regardless of the duration of the transmission, the frequency of transmission is related to the activity level. Consequently, even if there is no pressure data, the frequency of transmission provides activity data. Accordingly, some embodiments do not include a pressure sensor and provide only activity data.

Figure 2:
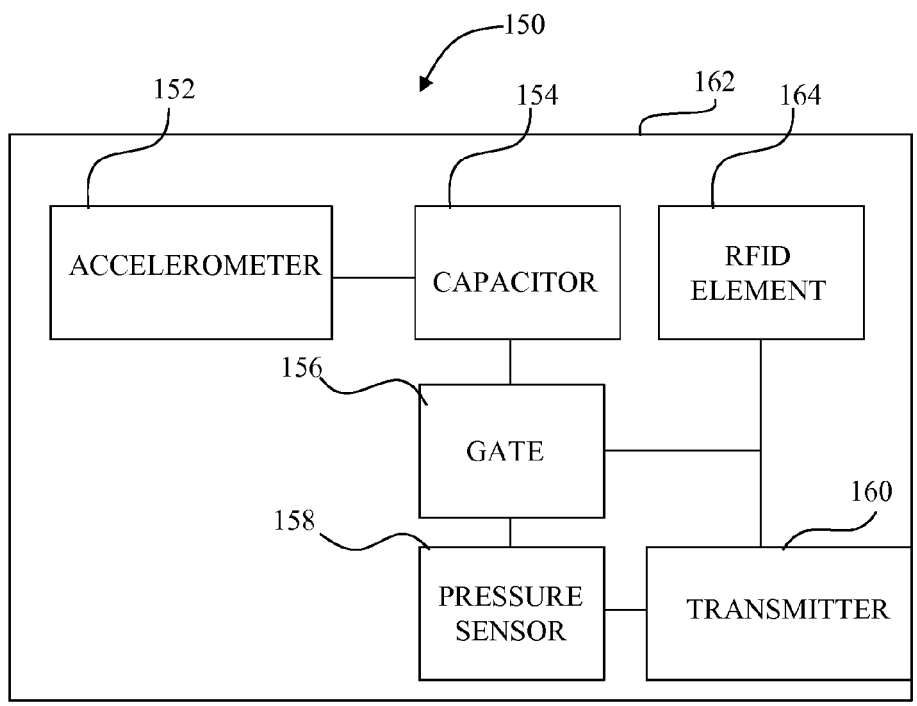
FIG. 2 depicts a block diagram illustrating an implantable pressure sensor assembly with an RFID element.

FIG. 2 depicts another embodiment of a pressure sensor assembly. The pressure sensor assembly 150 of FIG. 2 is similar to the pressure sensor 100 and includes an accelerometer 152, a capacitor 154, a gate element 156, a pressure sensor 158, and an RF transmitter 160 housed within a housing 162. The pressure sensor assembly 150 further includes an RFID element 164. The RFID element 164 may be an active or passive element. The RFID element 164 provides a unique identifier to the transmitter 110 which uniquely identifies the pressure sensor assembly 150. Accordingly, data transmitted by the transmitter 110 is uniquely associated with the individual even if multiple pressure sensor assemblies are transmitting.

While the above described embodiments include a transmitter which is powered by an internal component, in some embodiments the transmitter is powered by an external device. In such embodiments, a memory (not shown) may be provided. The data generated by the pressure sensor 108 is then stored in the memory along with a time stamp for later transmission. Some of these embodiments utilize a radio frequency identification (RFID) transmitter which is powered by an external device such as an RFID reader.

Figure 3:
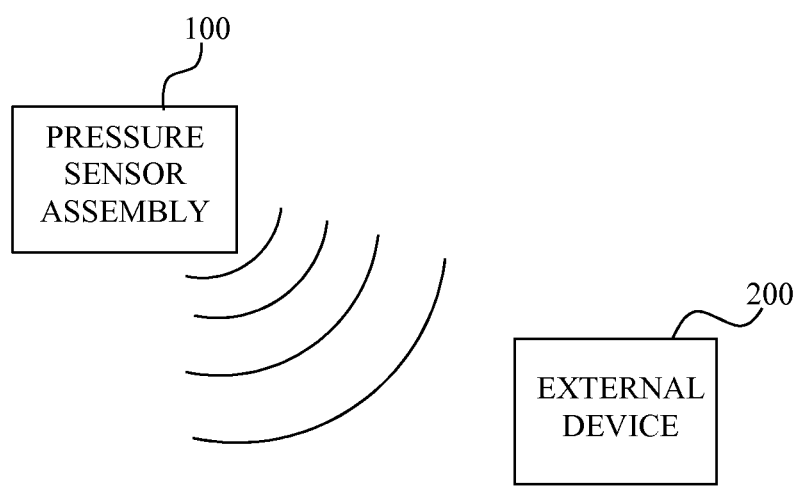
FIG. 3 depicts a block diagram of an implantable pressure sensor assembly communicating blood pressure and pressure sensor assembly identification data to an external device.

As noted above, the pressure sensor assemblies 100 and 150 are configured to transmit pressure data externally. For example, FIG. 3 depicts the pressure sensor assembly 100 wirelessly transmitting data to an external device 200. The external device 200 includes an RF receiver (not shown). In some embodiments, one or more of a memory for storing received data and a display for displaying the received data is included in the external device 200.

The external device 200 in one embodiment is configured to provide feedback to a user. For example, training program goals may be stored in the external device 200 and the feedback may provide details about deviation from the stored goals. In some embodiments, a training program is initially calibrated to the particular individual using interactive sessions. In the interactive session, specific activities are undertaken while the individual's activity level and blood pressure are monitored by the pressure sensor assembly 100. A baseline is thus established and used to establish training goals for the individual.

The external device 200 may further be used to monitor, map, and compare the user's data with reference data of a specialist trainer stored on the external device 200. The device 200 may further be configured to provide a health management report detailing energy burned, weight loss etc. Accordingly, the pressure sensor assembly is useful in a variety of applications where monitoring of an individual is desired.

Additionally, while FIG. 3 depicts a direct communication link between the pressure sensor assembly 100 and the external device 200, in some embodiments an intermediate device is used to transmit the data from the pressure sensor assembly 100 to the external device 200. For example, in embodiments wherein the external device is a server, a cellular phone, PDA, smartphone, or other fixed or mobile device may be configured to receive the data transmitted from the pressure sensor assembly 100 and retransmit the data to the external device 200. The user may then access the stored data through a network.

While the embodiments described above are directed to implantable devices, the devices need not be implanted. For example, the device may be configured to be strapped to an individual. Consequently, an individual about to begin an exercise period need only attach the pressure sensor assembly by, for example, positioning a wrist strap with an embedded pressure sensor assembly on the individual's wrist. The individual's activity level and blood pressure can then be monitored during the exercise period. At the completion of the exercise period, the individual simply removes the pressure sensor assembly.

In some embodiments, the pressure sensor assembly is integrated with a network of sensor devices to provide multiple physiological measurements. Each of the sensors may be provided with an energy harvesting system such as the accelerometer and capacitor of FIG. 1.

Figure 4:
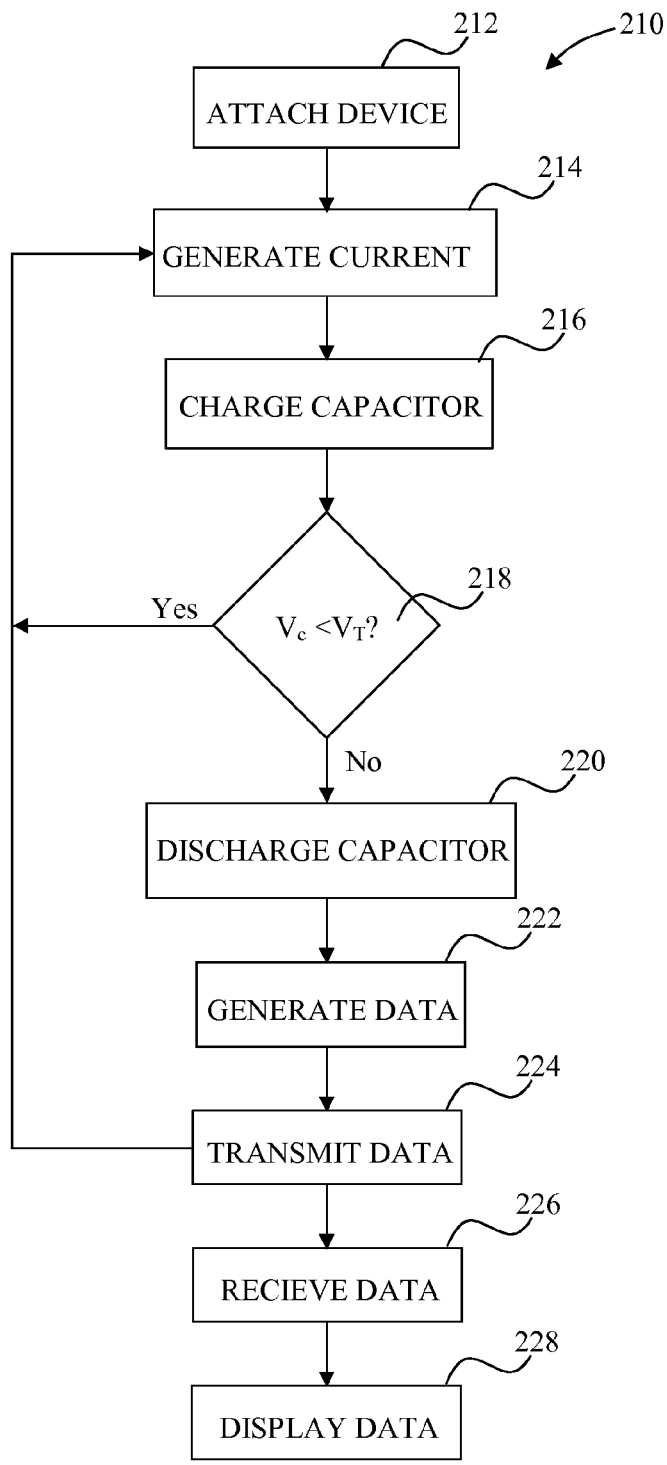
FIG. 4 depicts a flow chart of a method of measuring pressure using a pressure sensor assembly.

FIG. 4 depicts a process 210 for measuring activity and pressure of an individual using a pressure sensor assembly as described above. Initially, a pressure sensor assembly 100 is either implanted in an individual or otherwise attached to the individual (block 212). As the individual moves with the attached pressure sensor assembly 100, momentum changes cause the accelerometer 102 to generate bursts of electricity (block 214). The bursts of electricity charge the capacitor 104 (block 216).

As the capacitor voltage ($V_c$) increases, the gate element 106 checks the $V_c$ against a threshold voltage ($V_T$). Such "checking" may be a passive function of the gate element 106. If the $V_c$ is less than the $V_T$ (block 218), the process returns to block 214 and additional current is generated. If the $V_c$ is greater than or equal to the $V_T$, the process continues to block 220 and the gate element 106 automatically discharges the capacitor 104.

Upon discharge of the capacitor 220, the pressure sensor 108 is energized and generates a signal associated with the blood pressure of the individual (block 222). The generated signal is passed to the RF transmitter 110 and transmitted to an external device (block 224) as transmitted pressure data. In some embodiments, the transmitted signal includes a unique identified for the pressure sensor assembly 100. The process then continues to block 214.

Additionally, the transmitted data is received by an external device 200, time stamped, and stored (block 226). When desired, the stored data is displayed either by the external device 200 or at another user interface operably connected to the external device 200 (block 228). The displayed data includes the pressure data obtained from the pressure sensor 108 at block 222. Additionally, by comparing the time between received data (using the time stamps), activity data is generated and displayed.

The process 210 may be modified for different embodiments. For example, in embodiments which do not include a pressure sensor 108, block 222 is omitted. Accordingly, the external device 200 displays only activity data by comparing time stamps of received transmissions.

In embodiments with an internal memory, the data is time stamped and stored in the pressure sensor assembly 100 after block 222. The transmission of data (block 224) then occurs at a later time.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

The invention claimed is:

1. A pressure sensor assembly comprising:
an accelerometer configured to produce a first current upon movement of the accelerometer;
a capacitor configured to receive the first current thereby charging the capacitor;
a gate element operably connected to the capacitor and configured to discharge a second current from the capacitor upon the capacitor attaining a threshold voltage;
a pressure sensor configured to receive the discharged current to produce a first signal corresponding to at least one pressure reading of the pressure sensor; and
a transmitter operably connected to the pressure sensor and configured to transmit a second signal based upon the first signal to an external device configured to store data corresponding to the second signal.

2. The pressure sensor assembly of claim 1, wherein the accelerometer is a piezoelectric tri-axial accelerometer.

3. The pressure sensor assembly of claim 1, wherein the pressure sensor is a blood pressure sensor.

4. The pressure sensor assembly of claim 1, wherein the external device is configured to time stamp the second signal.

5. The pressure sensor assembly of claim 1, wherein the second signal includes identification data uniquely identifying the pressure sensor assembly.

6. The pressure sensor assembly of claim 1, wherein the pressure sensor is a low power pressure sensor.

7. The pressure sensor assembly of claim 1, wherein the transmitter is an RFID transmitter.

8. The pressure sensor assembly of claim 1, wherein the second signal comprises a discrete pressure data.

9. The pressure sensor assembly of claim 1, wherein the second signal comprises at least a full cycle of pressure data.

10. The pressure sensor assembly of claim 1, further comprising:
a housing configured to be implanted in an individual.

11. A method for measuring blood pressure by a pressure sensing assembly, comprising:
attaching a pressure sensing assembly with an accelerometer to an individual;
producing a first current with the accelerometer;
charging a capacitor with the first current;

automatically discharging a second current from the capacitor with a gate element when the capacitor reaches a predetermined voltage;

powering a pressure sensor with the second current to generate a first signal associated with at least one first pressure sensed by the pressure sensor;

transmitting a second signal based upon the first signal to an external device; and storing the second signal at the external device.

12. The method of claim 11, wherein storing the second signal comprises:

time stamping the second signal.

13. The method of claim 12, further comprising:

determining an activity level of the individual using the time stamp.

14. The method of claim 13, further comprising:

obtaining the at least one first pressure from the second signal;

comparing the obtained at least one first pressure to a baseline; and providing feedback to the individual based upon the comparison.

15. The method of claim 11, wherein transmitting a second signal comprises:

activating a radio frequency identification reader external to the pressure sensing assembly; and transmitting the second signal using an RFID transmitter.

16. The method of claim 15, further comprising:

storing the first signal in a memory in the pressure sensing assembly; and time stamping the stored first signal.

17. The method of claim 11, wherein the at least one first pressure comprises pressure data for a full cycle.

18. The method of claim 11, wherein attaching the pressure sensing assembly comprises:

implanting the pressure sensing assembly in the individual.

19. The method of claim 11, further comprising:

producing a third current with the accelerometer after transmitting the second signal;

charging the capacitor with the third current;

automatically discharging a fourth current from the capacitor with a gate element when the capacitor reaches a predetermined voltage after being charged with the third current;

powering the pressure sensor with the fourth current to generate a third signal associated with at least one second pressure sensed by the pressure sensor;

transmitting a fourth signal based upon the third signal to the external device; and storing the fourth signal at the external device.

20. The method of claim 19, further comprising:

time stamping the second signal with a first time stamp;

time stamping the fourth signal with a second time stamp; and determining an activity level of the individual based upon the time difference between the first time stamp and the second time stamp.

* * * * *